US00PP22148P2

(12) United States Plant Patent
Hofmann et al.

(10) Patent No.: US PP22,148 P2
(45) Date of Patent: Sep. 13, 2011

(54) ***PELARGONIUM* PLANT NAMED 'KUEGRAPURPI'**

(50) Latin Name: *Pelargonium crispum×Pelargonium grandiflorum*
Varietal Denomination: Kuegrapurpi

(75) Inventors: Christa Hofmann, Leipzig (DE); Klaus Olbricht, Dresden (DE); Katrin Meinl, Dresden (DE)

(73) Assignee: Kühne Jungpflanzen GbR Claus & Torsten Kühne, Dresden (DE)

( * ) Notice: Subject to any disclaimer, the term of this patent is extended or adjusted under 35 U.S.C. 154(b) by 0 days.

(21) Appl. No.: 12/798,341

(22) Filed: Mar. 31, 2010

(51) Int. Cl.
*A01H 5/00* (2006.01)

(52) U.S. Cl. ..... Plt./324

(58) Field of Classification Search ..... Plt./324
See application file for complete search history.

*Primary Examiner* — Susan McCormick Ewoldt
(74) *Attorney, Agent, or Firm* — C. A. Whealy

(57) ABSTRACT

A new and distinct cultivar of *Pelargonium* plant named 'Kuegrapurpi', characterized by its upright, somewhat outwardly spreading and mounded plant habit; compact and vigorous growth habit; freely branching habit; freely flowering habit; purple and light purple bi-colored flowers; no cooling treatment required for flower initiation and development; and good garden performance.

1 Drawing Sheet

Botanical designation: *Pelargonium crispum×Pelargonium grandiflorum.*

Cultivar denomination: 'KUEGRAPURPI'.

BACKGROUND OF THE INVENTION

The present invention relates to a new and distinct cultivar of *Pelargonium* plant, botanically known as *Pelargonium crispum×Pelargonium grandiflorum* and hereinafter referred to by the name 'Kuegrapurpi'.

The new *Pelargonium* plant is a product of a planned breeding program conducted by the Inventors in Dresden, Germany. The objective of the breeding program is to develop new interspecific *Pelargoniums* that can be grown as potted and/or bedding plants.

The new *Pelargonium* plant originated from a cross-pollination made by the Inventors in Dresden, Germany in 2006 of *Pelargonium crispum* 'Randy', not patented, as the female, or seed, parent with an unidentified selection of *Pelargonium grandiflorum,* not patented, as the male, or pollen, parent. The new *Pelargonium* plant was discovered and selected by the Inventors as a single flowering plant from within the progeny of the stated cross-pollination in a controlled greenhouse environment in Dresden, Germany in December, 2006.

Asexual reproduction of the new *Pelargonium* plant by vegetative terminal cuttings in a controlled greenhouse environment in Dresden, Germany since the spring of 2007, has shown that the unique features of this new *Pelargonium* plant are stable and reproduced true to type in successive generations.

SUMMARY OF THE INVENTION

Plants of the new *Pelargonium* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Kuegrapurpi'. These characteristics in combination distinguish 'Kuegrapurpi' as a new and distinct cultivar of *Pelargonium:*

1. Upright, somewhat outwardly spreading and mounded plant habit.
2. Compact and vigorous growth habit.
3. Freely branching habit; pinching is not required.
4. Freely flowering habit.
5. Purple and light purple bi-colored flowers.
6. No cooling treatment required for flower initiation and development.
7. Good garden performance.

Plants of the new *Pelargonium* differ primarily from plants of the female parent, 'Randy', in the following characteristics:

1. Plants of the new *Pelargonium* are more upright than and not as trailing as plants of 'Randy'.
2. Plants of the new *Pelargonium* have thicker stems, larger leaves and larger flowers than plants of 'Randy'.
3. Flowers of plants of the new *Pelargonium* are held closer together than flowers of plants of 'Randy'.
4. Plants of the new *Pelargonium* and 'Randy' differ in flower color as plants of 'Randy' have red purple and white bi-colored flowers.

Plants of the new *Pelargonium* differ primarily from plants of the male parent selection in the following characteristics:

1. Plants of the new *Pelargonium* are more compact than and not as vigorous as plants of the male parent selection.
2. Plants of the new *Pelargonium* have thinner stems, smaller leaves and smaller flowers than plants of the male parent selection.
3. Plants of the new *Pelargonium* flower earlier than plants of the male parent selection.
4. Plants of the new *Pelargonium* do not require a cooling treatment for flower initiation and development whereas plants of the male parent selection do require a cooling treatment for flower initiation and development.

Plants of the new *Pelargonium* can be compared to plants of the *Pelargonium grandiflorum* 'Cambi', disclosed in U.S. Plant Pat. No. 20,426. In side-by-side comparisons conducted in Dresden, Germany, plants of the new *Pelargonium* differed from plants of 'Cambi' in the following characteristics:

1. Plants of the new *Pelargonium* were more compact than and not as vigorous as plants of 'Cambi'.
2. Plants of the new *Pelargonium* had stronger lateral branches than plants of 'Cambi'.
3. Plants of the new *Pelargonium* were more freely flowering than plants of 'Cambi'.
4. Plants of the new *Pelargonium* had larger flowers than plants of 'Cambi'.

BRIEF DESCRIPTION OF THE PHOTOGRAPH

The accompanying colored photograph illustrates the overall appearance of the new *Pelargonium* plant showing the colors as true as it is reasonably possible to obtain in colored reproductions of this type. Colors in the photograph may differ slightly from the color values cited in the detailed botanical description which accurately describe the colors of the new *Pelargonium* plant. The photograph comprises a close-up view of a typical flowering plant of 'Kuegrapurpi' grown in a container.

DETAILED BOTANICAL DESCRIPTION

The aforementioned photograph and following observations, measurements and values describe plants grown 12-cm containers in Dresden, Germany in a glass-covered greenhouse during the summer and under conditions which closely approximate commercial *Pelargonium* production. During the production of the plants, day and night temperatures averaged 18° C. and light levels averaged 4,500 lux. Plants were 13 weeks old when the photograph and the description were taken. In the detailed description, color references are made to The Royal Horticultural Society Colour Chart, 2001 Edition, except where general terms of ordinary dictionary significance are used.

Botanical classification: *Pelargonium crispum*×*Pelargonium grandiflorum* 'Kuegrapurpi'.

Parentage:

*Female, or seed, parent.*—*Pelargonium crispum,* 'Randy' not patented.

*Male or pollen parent.*—Unidentified selection of *Pelargonium grandiflorum,* not patented.

Propagation:

*Type.*—By vegetative terminal cuttings.

*Time to initiate roots, summer.*—About 18 days at temperatures of 20° C.

*Time to initiate roots, winter.*—About 22 days at temperatures of 22° C.

*Time to produce a rooted young plant, summer.*—About 26 days at temperatures of 18° C.

*Time to produce a rooted young plant, winter.*—About 30 days at temperatures of 20° C.

*Root description.*—Fine, fibrous; creamy white in color.

*Rooting habit.*—Freely branching; dense.

Plant description:

*Plant/growth habit.*—Upright, somewhat outwardly spreading and mounded plant habit; inverted triangle; densely foliated; compact and vigorous growth habit; freely basal habit with about five to seven lateral branches developing per plant.

*Plant height, to top of umbels.*—About 23 cm.

*Plant height, to top of leaves.*—About 18 cm.

*Plant width.*—About 24 cm.

*Lateral branches.*—Length: About 7 cm. Diameter: About 3.5 mm. Internode length: About 2.5 cm. Strength: Strong. Texture: Pubescent. Color: Close to 141C.

Foliage description:

*Arrangement.*—Alternate; simple.

*Length.*—About 4.1 cm.

*Width.*—About 4.8 cm.

*Shape.*—Palmate, lobed.

*Apex.*—Cuspidate.

*Base.*—Obtuse.

*Margin.*—Serrate.

*Venation pattern.*—Palmate.

*Texture, upper and lower surfaces.*—Pubescent.

*Color.*—Developing leaves, upper surface: Close to 143A. Developing leaves, lower surface: Close to 144B. Fully expanded leaves, upper surface: Close to 138A; venation, close to 138A. Fully expanded leaves, lower surface: Close to 139C; venation, close to 139C. Petiole: Length: About 1.5 cm. Diameter: About 2 mm. Texture, upper and lower surfaces: Smooth, glabrous. Color, upper and lower surfaces: Close to 141C.

Flower description:

*Flower arrangement.*—Single rotate flowers arranged in umbels arising from apical leaf axils; umbels displayed above the foliage on moderately strong peduncles; flowers face mostly upright to outwardly.

*Fragrance.*—Slightly fragrant, aromatic.

*Quantity of flowers.*—Freely flowering habit; about ten flowers develop per umbel and about 15 umbels per plant.

*Flowering season.*—In Germany, flowering initiates in the spring and continues until the autumn; plants do not require a cooling treatment for flower initiation and development; early flowering habit, plants begin flowering about 60 days after planting.

*Flower longevity.*—Individual flowers last about six days on the plant; flowers not persistent.

*Umbel height.*—About 7 cm.

*Umbel diameter.*—About 8 cm.

*Flower diameter.*—About 5.5 cm by 5.5 cm.

*Flower depth (height).*—About 2 cm.

*Flower buds.*—Length: About 1.5 cm. Diameter: About 6 mm. Shape: Ovoid. Color: Close to 138A.

*Petals.*—Quantity per flower: Five arranged in a single whorl. Length: About 3.3 cm to 3.6 cm. Width: About 2 cm to 3 cm. Shape: Obovate. Apex: Rounded. Base: Attenuate. Margin: Entire. Texture, upper and lower surfaces: Smooth, glabrous. Color: When opening and fully opened, upper surface: Close to N79B; towards the margins, close to 76B; venation, close to N74A. When opening and fully opened, lower surface: Close to N79C; towards the margins, close to 76C; venation, close to N74B.

*Sepals.*—Quantity per flower: Five arranged in a single whorl. Length: About 1.5 cm. Width: About 5 mm. Shape: Lanceolate. Apex: Acuminate. Base: Obtuse. Margin: Entire. Texture, upper and lower surfaces: Smooth, glabrous. Color, upper surface: Close to 138A. Color, lower surface: Close to 138B.

*Peduncle* (*umbel stem*).—Length: About 4 cm. Diameter: About 2 mm. Strength: Moderately strong. Angle: Mostly erect. Texture: Smooth, glabrous. Color: Close to 138A.

*Pedicel* (*individual flower stem*).—Length: About 2.2 cm. Diameter: About 1.5 mm. Strength: Moderately strong. Angle: Mostly erect. Texture: Smooth, glabrous. Color: Close to 138B.

*Reproductive organs.*—Androecium: Stamen quantity per flower: About seven. Filament length: About 1.3 cm. Filament color: Close to 155B. Anther length: About 2 mm. Anther shape: Ovate. Anther color: Close to 12D. Pollen amount: No pollen observed. Gynoecium: Pistil quantity per flower: One. Pistil length: About 1.5 cm. Stigma shape: Five-parted. Stigma color: Close to N78A. Style length: About 1 cm. Style color: Close to 71B. Ovary color: Close to 130D.

*Seeds/fruits.*—Seed and fruit development has not been observed on plants of the new *Pelargonium.*

Disease/pest resistance: Plants of the new *Pelargonium* have been observed to be resistant to *Xanthomonas campestris* pv. *pelargonii* and *Puccinia pelargonii-zonalis.* Plants of the new *Pelargonium* have not been observed to be resistant to pests and other pathogens common to *Pelargoniums.*

Garden performance: Plants of the new *Pelargonium* have been observed to have good garden performance and to tolerate wind, rain and temperatures ranging from about 5° C. to about 40° C.

It is claimed:

1. A new and distinct *Pelargonium* plant named 'Kuegrapurpi' as illustrated and described.

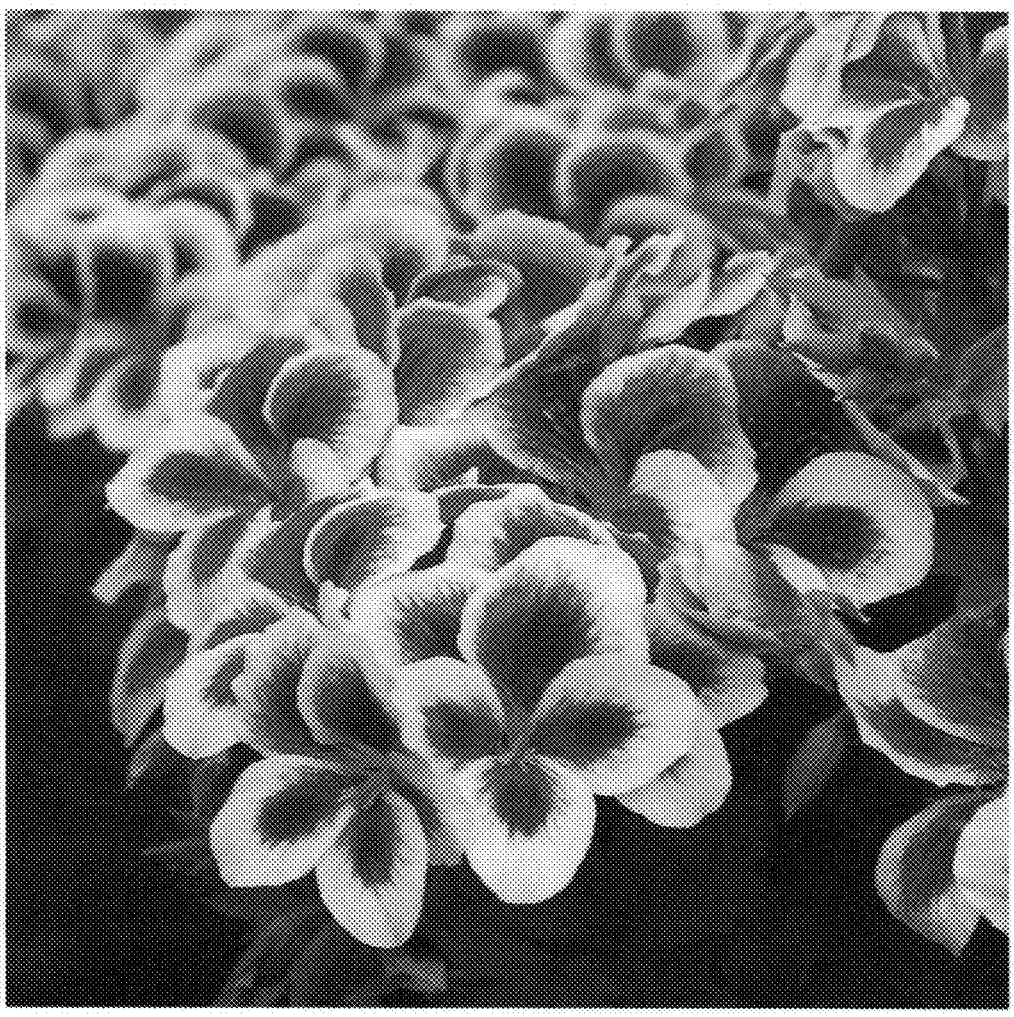

* * * * *